United States Patent [19]

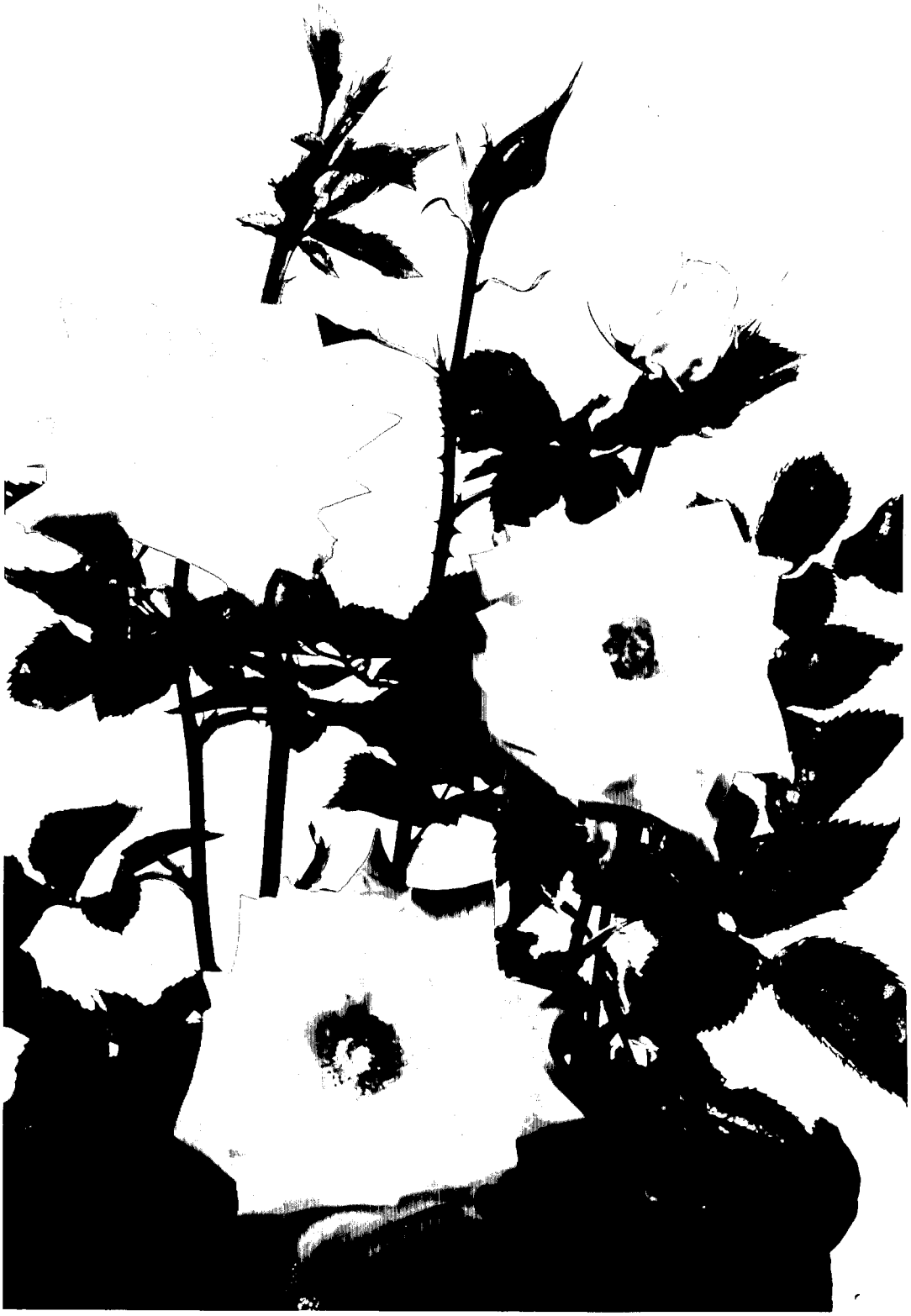

Christensen

[11] Patent Number: Plant 5,558

[45] Date of Patent: Sep. 17, 1985

[54] HYBRID TEA ROSE CV. AROKUNCE

[75] Inventor: Jack E. Christensen, Ontario, Calif.

[73] Assignee: Armstrong Nurseries, Inc., Ontario, Calif.

[21] Appl. No.: 557,892

[22] Filed: Dec. 5, 1983

[51] Int. Cl.[4] ..... A01H 5/00

[52] U.S. Cl. ..... Plt./17

[58] Field of Search ..... Plt./11, 17

*Primary Examiner*—James R. Feyrer

*Attorney, Agent, or Firm*—Synnestvedt & Lechner

[57] ABSTRACT

A new hybrid tea rose for cut flowers and garden decoration, having as its seed parent Zorina (U.S. Plant. Pat. No. 2,321) and as its pollen parent Yankee Doodle (U.S. Plant Pat. No. 3,957). The new cultivar produces an abundance of orange blended flowers, has very vigorous growth, is easy to grow, and has well-above-average disease resistance. Its nearly continual production of long-lasting flowers borne on cutting-length stems lend it well to providing bouquets for the home, and its bushy habit and abundant foliage make it an attractive plant in the garden.

1 Drawing Figure

This invention relates to a new class of Hybrid Tea Rose cv. AROKUNCE. The plant is an outdoor seedling of the medium-to-tall bush type, cultivated for cut flowers and garden decoration. The plant's hardiness is as yet untested. It was propagated by budding by Jack E. Christensen in Ontario, Calif., having as its seed parent ZORINA (U.S. Plant Pat. No. 2,321) and as its pollen parent YANKEE DOODLE (U.S. Plant Pat. No. 3,957).

The new rose plant cv. Arokunce is particularly characterized by the following combination of characteristics: its abundant production of orange blended flowers, essentially as described and illustrated; its vigorous growth; its ease of growth; its well-above-average disease resistance, which lends to its ease of growth; its nearly continual production of long-lasting flowers borne on cutting-length stems, which lend well to providing bouquets for the home; and its bushy habit and abundant glossy foliage, which make it an attractive plant in the garden. It holds these distinguishing characteristics through succeeding propagations by budding.

This new rose may be distinguished from its seed parent Zorina (U.S. Plant Pat. No. 2,321) by the following combination of characteristics: Arokunce is useful only for garden decoration, whereas the seed parent is predominantly used for greenhouse cut-rose production. The seed parent usually bears more than one flower per stem, whereas the new rose Arokunce bears most flowers one to a stem. Whereas the seed parent bears flowers with about 25 petals, the new rose bears flowers of significantly higher petalage (30 to 33). The new seedling bears flowers of a 3- to 4-inch diameter, whereas Zorina bears significantly smaller flowers, 2½ to 3 inches in diameter.

The new cultivar rose Arokunce may be distinguished from its pollen parent Yankee Doodle (U.S. Plant Pat. No. 3,957) by the following combination of characteristics: Yankee Doodle bears flowers of a coloration that combines yellow, pink, and orange, whereas the new rose bears flowers of a blended coloration of predominantly orange and red tones, essentially as described and illustrated herein. Whereas the new rose usually bears flowers with 30 to 33 petals, Yankee Doodle bears flowers of a significantly higher petalage, 65 to 75 petals. The new rose bears flowers of 3- to 4-inch diameter, whereas Yankee Doodle bears flowers of significantly larger diameter (4½ to 5 inches). Whereas Yankee Doodle produces a tall, upright bush, the new rose produces a significantly shorter, more spreading bush.

FLOWER

The new variety usually bears its flowers singly, sometimes 2 to 3 flowers per stem in irregular clusters, on strong stems that are of medium length for the class. Outdoors, the plant blooms nearly continuously and in very abundant quantities during the growing season. It has a slight tea fragrance.

The accompanying drawing illustrates the plant in color and shows the flowering thereof from bud to full bloom.

Throughout this specification, color names beginning with a small letter signify that the name of that color as used in common speech is aptly descriptive. Color names beginning with a capital letter designate values based upon The R.H.S. Colour Chart of The Royal Horticultural Society in London, England.

BUD

The peduncle is of short to average length for the class and of average to heavy caliper, strong and erect. It is moderately smooth with some stipitate glands and between Yellow-Green 146A and Yellow-Green 147A in coloration.

Before the calyx breaks, the bud is small to medium in size for the class and of medium length, pointed and ovoid in form, with few foliaceous appendages and stipitate glands on the surface of the bud. There are usually slender, shallowly serrate, foliaceous parts extending beyond the tip of the bud equal to three-quarters or more of its length.

As the calyx breaks, the bud color is between Red 43A and Red 45A.

The inner surface of the sepals has a fine, woolly tomentum; margins are lined with stipitate glands and hairs.

As the first petal opens, the bud is small to average in size for the class, of medium length and ovoid to pointed in form. The color on the outside at the basal attachment zone is near Yellow 9A, gradually suffusing to between Orange 24B and Orange-Red 31B. Areas that are exposed to sunlight blush as deeply as between Orange-Red 34A and Red 45A. The color on the inside at the basal attachment zone is near Yellow 9A, gradually suffusing to between Orange-Red 32B and Orange 26B. Areas near the petal edge that are exposed to sunlight blush as deeply as between Orange-Red 34A and Red 45A. The bud opens up well and is not prevented from opening or destroyed by cold, hot, wet, or dry weather.

BLOOM

The size of the bloom when fully open is small to average for the class, ranging from 3 to 4 inches. The petalage is double, with from 30 to 33 petals and from 1 to 3 petaloids; the petals are arranged regularly. The bloom form when half open is moderately high-centered to full. The petals are moderately cupped, with the petal edges very reflexed to quilled outward. when fully open, the bloom is moderately full with petals loosely cupped and petal edges reflexed to quilled outward.

The petals are moderately heavy to crisp, of medium thickness, and with the inside slightly shiny and the outside slightly satiny. The outside and intermediate petals are broadly obovate, with a rounded apex. The inside petals are nearly round to broadly obovate and have a rounded apex. The colors may be modified by being bordered or margined or shaded or washed or tinted with other colors.

The paragraph immediately following describes the color values observed in a flower newly opened in the month of July. The plant described had been grown outdoors in Ontario, Calif.

The outside surface of the outside petals has a basal attachment zone near Yellow 6B, gradually deepening to between Orange 24B and Orange 26B. Areas that are exposed to sunlight blush as deeply as between Orange-Red 34A and Red 45A. The inside surface of the outside petals has a basal attachment zone near Yellow 6B which gradually deepens to between Orange 26B and Orange-Red 32C. Areas exposed to sunlight blush as deeply as between Orange-Red 34A and Red 45A. The outside surface of the intermediate petals is the same as the outside surface of the outside petals with very little blushing. The inside surface of the intermediate petals is the same as the inside surface of the outside petals with much less blushing. The outside and inside surfaces of the inner petals are the same as the outside and inside surfaces described above, but with no blushing.

The paragraph immediately following describes color values observed in a bloom which had been open for three days in the month of July. The plant described had been grown outdoors in Ontario, Calif.

The outside surface of the outside petals has a basal attachment zone near Yellow 10B which deepens to between Orange-Red 35D and Red 41B. Areas that are exposed to sunlight blush as deeply as between Red 39A and Red 43C. The inside surface of the outside petals has a basal attachment zone near Yellow 10B which quickly deepens to between Red 41C and Orange-Red 35B. When exposed to sunlight, the majority of the petal blushes to between Red 40A and Red 45A. The outside and inside surfaces of the inside petals have the same color as the outside and inside surfaces of the outside petals, except that the outside surface of the inside petals does not blush.

The general color effect of the newly opened flower is predominantly between Orange 26B and Orange-Red 32C. The edges of the outermost petals are between Orange-Red 34A and Red 45A. After being open three days, the bloom gives a general color effect which is between Red 40A and Red 45A. The petals usually drop off cleanly and are not particularly affected by cold, hot, wet, or dry weather.

In July, roses grown in the garden last on the bush from 4 to 5 days; cut roses grown outdoors and kept at livingroom temperatures will last from 5 to 6 days.

REPRODUCTIVE ORGANS

An average number of stamens are arranged regularly about the pistils.

The filaments are of a short to medium length. Many have anthers.

The anthers are of small size, and all open approximately at once. Their color when immature is near Yellow 10A and when mature, between Greyed-Orange 165A and Greyed-Orange 166A.

Pollen is moderate in quantity and near Yellow 10A in color.

Pistils are average to many in number (approximately 70).

The styles are uneven, short to average in length, of thin to average caliper, and somewhat bunched.

The stigma is near Yellow 2C in color.

This variety as grown in Ontario, Calif., does not normally set hips.

FOLIAGE

The compound leaves are borne very abundantly and usually comprise from 3 to 5 leaflets. The leaves are of medium size for the class, heavy to somewhat leathery, and glossy. The leaflets are nearly oval in shape and have an acute apex and a round to acute base. The margin is irregularly serrate.

The mature foliage displays upon its upper surface a color which is between Green 139A and Yellow-Green 147A. The under surface is near Yellow-Green 147B.

The upper surface of the young foliage is between Greyed-Purple 187B and Greyed-Purple 183A. Its under surface is also between Greyed-Purple 187B and Greyed-Purple 183A.

The rachis is of average size, grooved on its upper side, with some stipitate glands on the edges. The underside is sparsely prickly and with stipitate glands.

The stipules are medium to long in length, moderately narrow with medium-length points, usually turning out at an angle of more than 45 degrees.

The plant displays a more-than-average resistance to mildew, rust, and blackspot as compared to other commercial varieties grown under comparable conditions in Ontario, Calif.

GROWTH

The plant is of medium height, bushy, upright and spreading in habit, and is much branched. It displays very vigorous growth. The canes are of medium caliper for the class.

The main stems are near Yellow-Green 146C in color. They bear several large prickles which are moderately short for the class. The prickles are almost straight and have a medium-length, moderately narrow base. Prickle color is near Greyed-Orange 165C. There are several small prickles of near Greyed-Orange 165C coloration. There are no hairs.

The branches are of a color between Green 138A and Green 139C. They bear several large prickles which are of moderately short length for the class. The large prickles are almost straight and have a medium-length, moderately narrow base. The prickles have a color near Greyed-Yellow 160B. The branches have several small prickles, of the same color as the large prickles, and no hairs.

New shoots are between Greyed-Purple 183A and Greyed-Purple 187B in color. They bear several to many large prickles which are of moderately short length for the class, almost straight, and having a medium-length, moderately narrow base. Large prickles are between Greyed-Purple 183A and Greyed-Purple 187B in color. There are many small prickles and few hairs, all between Greyed-Purple 183A and Greyed-Purple 187B in color.

I claim:

1. A new and distinct variety of rose plant of the hybrid tea class, substantially as herein shown and described, being particularly characterized by its abundant production of orange blended flowers, essentially as described and illustrated; its vigorous growth; its ease of growth; its well-above-average disease resistance; its nearly continual production of long-lasting flowers borne on cutting-length stems; and its bushy habit and abundant glossy foliage, which make it an attractive plant in the garden.

* * * * *